United States Patent
Haye et al.

(10) Patent No.: US 11,371,979 B2
(45) Date of Patent: Jun. 28, 2022

(54) MULTI-PASSAGE OIL DEBRIS MONITOR TO INCREASE DETECTION CAPABILITY IN HIGH OIL FLOW SYSTEMS

(71) Applicant: United Technologies Corporation, Farmington, CT (US)

(72) Inventors: Sheridon Everette Haye, Mansfield, CT (US); Edward Thomas Rocco, Rocky Hill, CT (US)

(73) Assignee: Raytheon Technologies Corporation, Farmington, CT (US)

( * ) Notice: Subject to any disclaimer, the term of this patent is extended or adjusted under 35 U.S.C. 154(b) by 427 days.

(21) Appl. No.: 16/456,420

(22) Filed: Jun. 28, 2019

(65) Prior Publication Data

US 2020/0408733 A1    Dec. 31, 2020

(51) Int. Cl.
*F16N 29/00* (2006.01)
*G01N 33/28* (2006.01)
*G01N 15/06* (2006.01)
*F01M 1/18* (2006.01)
*F01D 25/18* (2006.01)
*G01N 15/00* (2006.01)
*F16N 39/06* (2006.01)

(52) U.S. Cl.
CPC ......... *G01N 33/2888* (2013.01); *F01D 25/18* (2013.01); *F01M 1/18* (2013.01); *F16N 29/00* (2013.01); *G01N 15/0656* (2013.01); *G01N 33/2858* (2013.01); *F05D 2220/32* (2013.01); *F05D 2260/83* (2013.01); *F05D 2260/98* (2013.01); *F16N 39/06* (2013.01); *F16N 2200/04* (2013.01); *F16N 2210/02* (2013.01); *G01N 2015/0053* (2013.01)

(58) Field of Classification Search
CPC ....... F01D 25/18; F01M 1/18; F05D 2220/32; F05D 2260/83; F05D 2260/98; F16N 29/00; F16N 2200/04; G01N 15/0656; G01N 33/2858; G01N 33/2888; G01N 2015/0053

See application file for complete search history.

(56) References Cited

U.S. PATENT DOCUMENTS

| | | | |
|---|---|---|---|
| 4,837,511 A * | 6/1989 | Whittington | G01V 3/102 324/204 |
| 5,001,424 A * | 3/1991 | Kellett | F16N 29/00 324/204 |
| 5,811,664 A * | 9/1998 | Whittington | G01V 3/101 73/53.07 |
| 8,226,822 B2 | 7/2012 | Paradise | |
| 2006/0152213 A1* | 7/2006 | Thompson | G01N 27/023 324/204 |
| 2008/0250851 A1* | 10/2008 | Keller | G01N 33/2888 73/114.55 |

(Continued)

*Primary Examiner* — Eric S. McCall
(74) *Attorney, Agent, or Firm* — Bachman & LaPointe, P.C.

(57) ABSTRACT

An oil debris monitoring sensor includes a multiple of passages within the housing, each of the multiple of passages surrounded by a set of coils to detect a particle. A method for determining a presence of a particle in a system includes a) installing a single sensor in-line with an oil flow path; b) communicating oil through a multiple of passages within the housing of the single sensor; c) detecting a particle through the single sensor; and d) isolating the particle to one of the multiple of passages within the sensor housing.

15 Claims, 10 Drawing Sheets

(56) References Cited

U.S. PATENT DOCUMENTS

| | | | |
|---|---|---|---|
| 2013/0000376 A1* | 1/2013 | Allam | G01N 33/2858 73/1.02 |
| 2015/0293009 A1* | 10/2015 | Henning | G01N 15/1463 356/72 |
| 2016/0017747 A1 | 1/2016 | Parnin et al. | |
| 2018/0030850 A1* | 2/2018 | Hagen | F16N 29/04 |
| 2020/0264157 A1* | 8/2020 | Rocco | G01N 15/1031 |

\* cited by examiner

MULTI-PASSAGE OIL DEBRIS MONITOR TO INCREASE DETECTION CAPABILITY IN HIGH OIL FLOW SYSTEMS

BACKGROUND

The present disclosure relates to an oil system for rotating machinery such as a gas turbine engine and, more particularly, to a multi-passage oil debris monitoring sensor.

Many types of mechanical machinery include various components that require lubrication. Gas turbine engines, for example, typically include gears and bearings that require a lubricating liquid, such as oil, for lubrication and cooling during operation. When an oil wetted component has a mechanical failure, metallic debris may be released into the lubricating liquid. In order to receive advanced warning of these mechanical systems failures for the purpose of condition-based maintenance, lubrication systems may include an oil debris monitoring system to sense metallic debris in the oil. An oil debris monitor system is used to flag the initiation or progression of mechanical failures in the lubricated mechanical machinery.

Metallic debris, measured by the counts and mass of particles detected by the oil debris monitor, is processed and monitored by a controller, and when debris is released at a critical rate, an alert is produced, driving field troubleshooting and corrective action. While oil debris monitor sensing technology is well developed, application of this technology in aerospace systems, such as gas turbine engines, is much challenged due to the stringent requirements on fault detection and the environment.

Today's aerospace systems are often built with great sophistication and little margin, which requires fault detection to be early, accurate and reliable. For mechanical failures in gas turbine engine applications, detection of fine particles (a few hundred microns) is required. The operating environment (vibration, pressure pulsations, aeration, etc.) can induce noise in oil debris monitor signals. Furthermore, the ODM sensor detection capability is defined by signal to noise ratio (SNR). SNR is defined by sensor oil flow bore cross sectional area for a given particle size. As thrust requirements for engine scale upward, the oil flow requirement also increases to ensure adequate system cooling. To prevent an ODM sensor from choking the system as oil flow increases, sensor bore has historically been increased to fit into the lubrication system. A sensor with an increased bore, however, will eventually no longer be able to detect small particles and the SNR for the same sized particle will continually decrease as bore size increases. This may also prevent enough debris in a failure mode from being detected for effective condition-based maintenance capability. A potential solution to this problem would be to install two ODM sensors in the system in parallel. Although this method can be used to meet the detection requirements for a system, it also doubles the weight, cost, and complexity of the sensors and harnesses, and plumbing. Furthermore, the scalability of this concept is limited (i.e., three or more sensors becomes exceedingly uneconomical).

SUMMARY

An oil debris monitoring sensor according to one disclosed non-limiting embodiment of the present disclosure includes a multiple of passages within a housing, each of the multiple of passages surrounded by a set of coils required for particle detection.

A further embodiment of any of the foregoing embodiments of the present disclosure includes that the multiple of passages within the housing includes two or more passages.

A further embodiment of any of the foregoing embodiments of the present disclosure includes that a first set of coils around a first passage of the multiple of passages are wound in a different direction than a second set of coils around a second passage of the multiple of passages.

A further embodiment of any of the foregoing embodiments of the present disclosure includes a dielectric between the first passage and the second passage.

A further embodiment of any of the foregoing embodiments of the present disclosure includes that each set of coils includes a respective first field coil, a sensor coil, and a second field coil.

A further embodiment of any of the foregoing embodiments of the present disclosure includes that the housing is located in-line with an oil flow path that is in communication with a geared architecture of a gas turbine engine.

An oil debris monitoring sensor according to one disclosed non-limiting embodiment of the present disclosure includes a first passage within a housing along a first axis; a first field coil, a sensor coil, and a second field coil around the first passage and along the first axis; a second passage within the housing along a second axis parallel to the first axis; and a first field coil, a sensor coil, and a second field coil around the second passage and along the second axis.

A further embodiment of any of the foregoing embodiments of the present disclosure includes that the housing is located in-line with an oil flow path that is in communication with a geared architecture of a gas turbine engine.

A further embodiment of any of the foregoing embodiments of the present disclosure includes that a first magnetic field generated by the first field coil around the first passage is in a first direction and a second magnetic field generated by the first field coil around the second passage is in a second direction opposite the first direction.

A further embodiment of any of the foregoing embodiments of the present disclosure includes a dielectric between the first passage and the second passage.

A method for determining a presence of a particle in a system according to one disclosed non-limiting embodiment of the present disclosure includes: a) locating a housing in-line with an oil flow path; b) communicating oil through a multiple of passages within the housing; c) detecting a particle through processing data from each passage; and d) isolating the particle to one of the multiple of passages within the housing.

A further embodiment of any of the foregoing embodiments of the present disclosure includes locating the oil flow path in communication with a geared architecture of a gas turbine engine.

A further embodiment of any of the foregoing embodiments of the present disclosure includes that step d) includes generating a first magnetic field around a first passage in a first direction and generating a second magnetic field around a second passage in a second direction opposite the first direction.

A further embodiment of any of the foregoing embodiments of the present disclosure includes that step d) includes determining an interference between a magnetic field associated with a first passage and a magnetic field associated with a second passage in response to the particle passing through the housing.

A further embodiment of any of the foregoing embodiments of the present disclosure includes that step d) includes applying a channel isolation algorithm if a minimum voltage is not identified in response to the particle passing through the housing.

A further embodiment of any of the foregoing embodiments of the present disclosure includes that step d) includes applying a channel isolation algorithm if a minimum voltage is not identified.

A further embodiment of any of the foregoing embodiments of the present disclosure includes that step d) includes determining whether a minimum amplitude in a second passage is within a predetermined range, and assessing whether a second particle is passing through the second passage.

The foregoing features and elements may be combined in various combinations without exclusivity, unless expressly indicated otherwise. These features and elements as well as the operation thereof will become more apparent in light of the following description and the accompanying drawings. It should be appreciated; however, the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
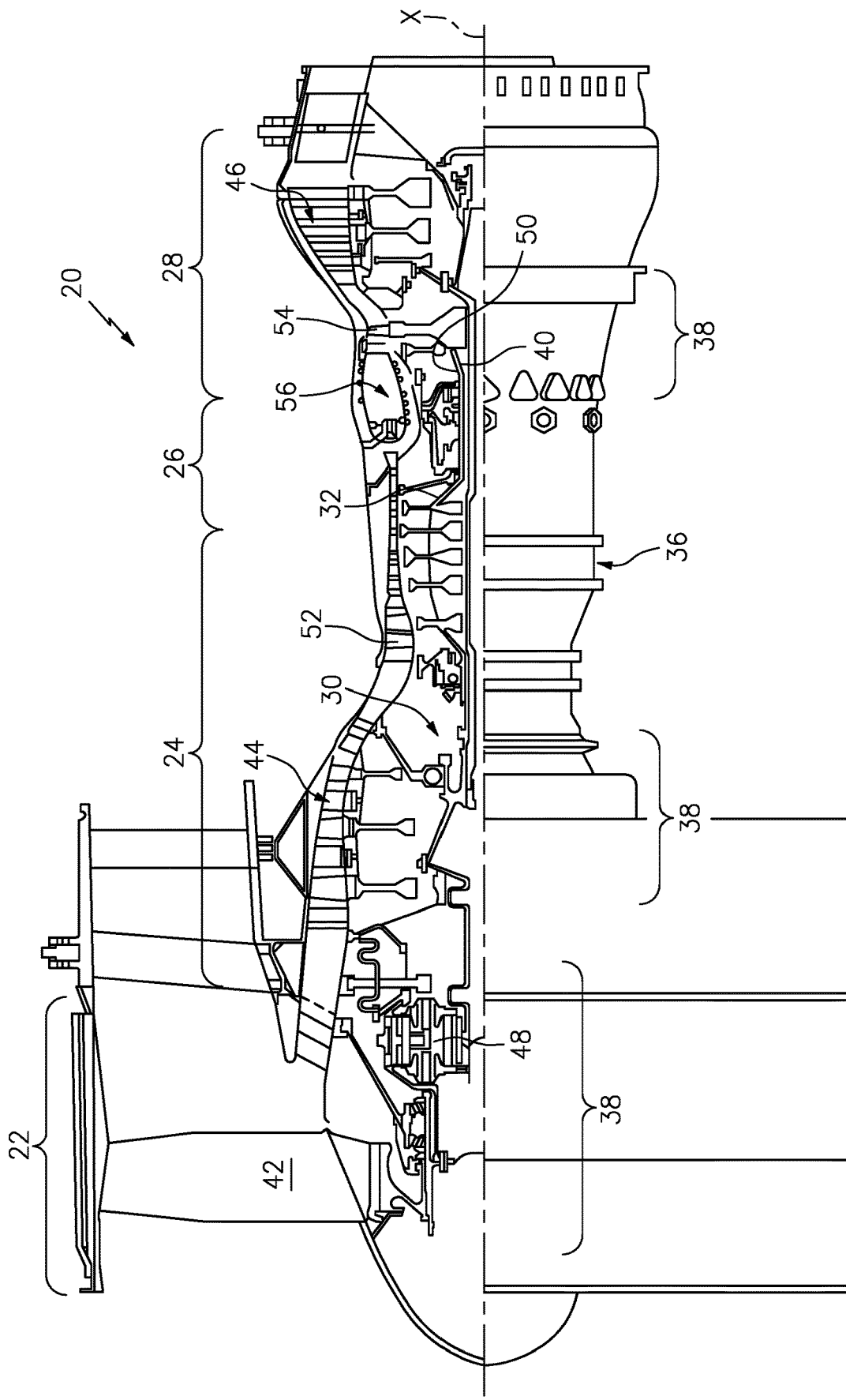
FIG. 1 is a schematic cross-section of an example gas turbine engine architecture.

FIG. 1 schematically illustrates a gas turbine engine 20. The gas turbine engine 20 is disclosed herein as a two-spool turbofan that generally incorporates a fan section 22, a compressor section 24, a combustor section 26, and a turbine section 28. The fan section 22 drives air along a bypass flowpath while the compressor section 24 drives air along a core flowpath for compression and communication into the combustor section 26, then expansion through the turbine section 28. Although depicted as a turbofan in the disclosed non-limiting embodiment, it should be appreciated that the concepts described herein may be applied to other engine architectures such as turbojets, turboshafts, and three-spool (plus fan) turbofans.

The engine 20 generally includes a low spool 30 and a high spool 32 mounted for rotation about an engine central longitudinal axis X relative to an engine static structure 36 via several bearings 38. The low spool 30 generally includes an inner shaft 40 that interconnects a fan 42, a low pressure compressor ("LPC") 44 and a low pressure turbine ("LPT") 46. The inner shaft 40 drives the fan 42 directly or through a geared architecture 48 that drives the fan 42 at a lower speed than the low spool 30. An exemplary reduction transmission is an epicyclic transmission, such as a planetary or star gear system.

The high spool 32 includes an outer shaft 50 that interconnects a high pressure compressor ("HPC") 52 and high pressure turbine ("HPT") 54. A combustor 56 is arranged between the high pressure compressor 52 and the high pressure turbine 54. The inner shaft 40 and the outer shaft 50 are concentric and rotate about the engine central longitudinal axis X which is collinear with their longitudinal axes.

Core airflow is compressed by the LPC 44, then the HPC 52, mixed with the fuel and burned in the combustor 56, then expanded over the HPT 54 and the LPT 46 which rotationally drive the respective high spool 32 and the low spool 30 in response to the expansion. The shafts 40, 50 are supported at a plurality of points by bearings 38 within the static structure 36.

Figure 2:
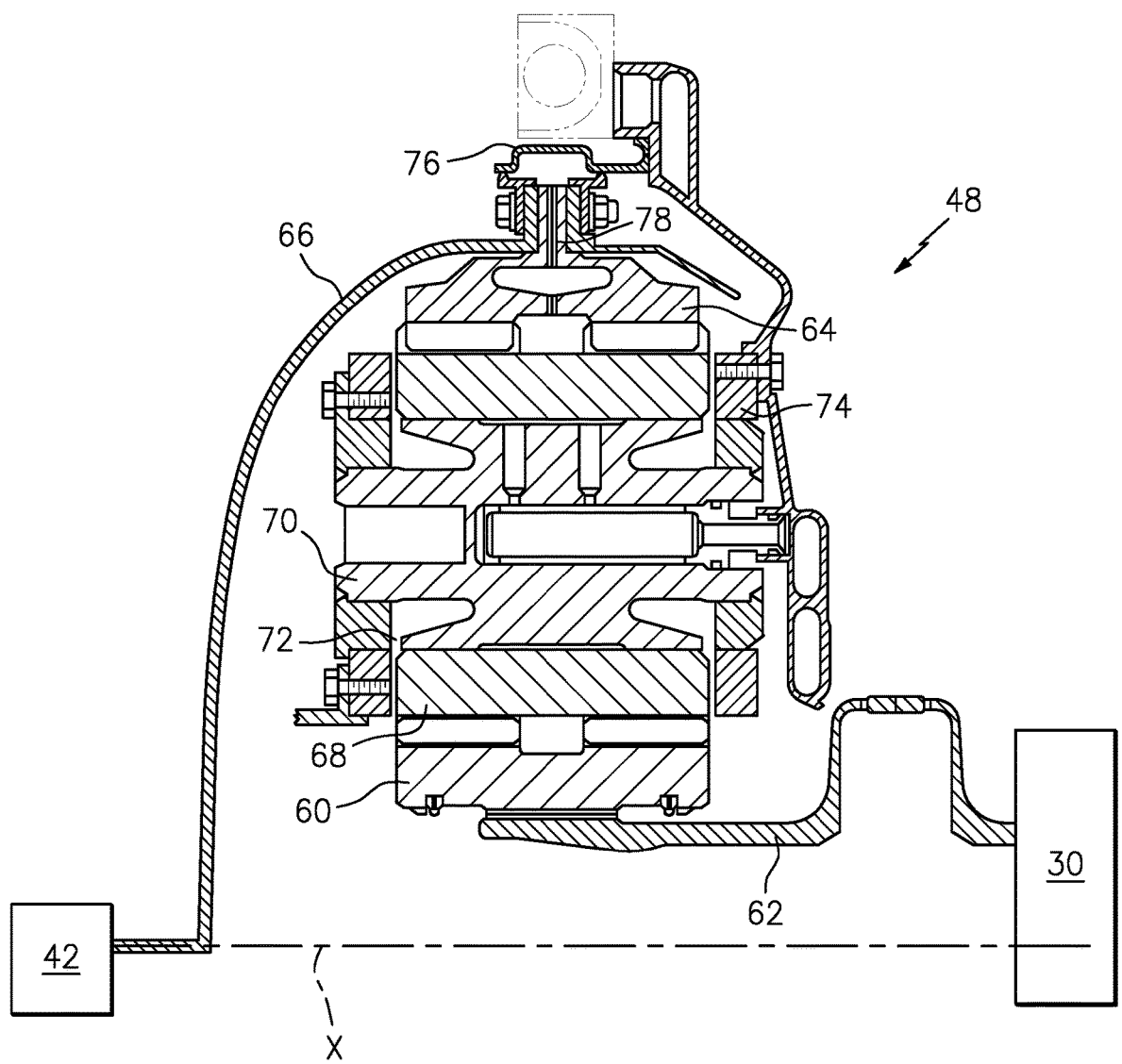
FIG. 2 is a schematic cross-section of a geared architecture for a gas turbine engine.

With reference to FIG. 2, the geared architecture 48 includes a sun gear 60 driven by a sun gear input shaft 62 from the low spool 30, a ring gear 64 connected to a ring gear output shaft 66 to drive the fan 42 and a set of intermediate gears 68 in meshing engagement with the sun gear 60 and ring gear 64. Each intermediate gear 68 is mounted about a journal pin 70 which are each respectively supported by a carrier 74. The input shaft 62 and the output shaft 66 counter-rotate as the sun gear 60 and the ring gear 64 are rotatable about the engine central longitudinal axis X. The carrier 74 is grounded and non-rotatable even though the individual intermediate gears 68 are each rotatable about their respective axes 80. An oil recovery gutter 76 is located around the ring gear 64. The oil recovery gutter 76 may be radially arranged with respect to the engine central longitudinal axis X.

A replenishable film of oil, not shown, is supplied to an annular space 72 between each intermediate gear 68 and the respective journal pin 70. One example applicable oil meets U.S. Military Specification MIL-PRF-23699, for example, Mobil Jet Oil II manufactured by ExxonMobil Aviation, United States. Oil is supplied through the carrier 74 and into each journal pin 70 to lubricate and cool the gears 60, 64, 68 of the geared architecture 48. Once communicated through the geared architecture 48 the oil is radially expelled through the oil recovery gutter 76 in the ring gear 64 by various paths such as oil passage 78.

Figure 3:
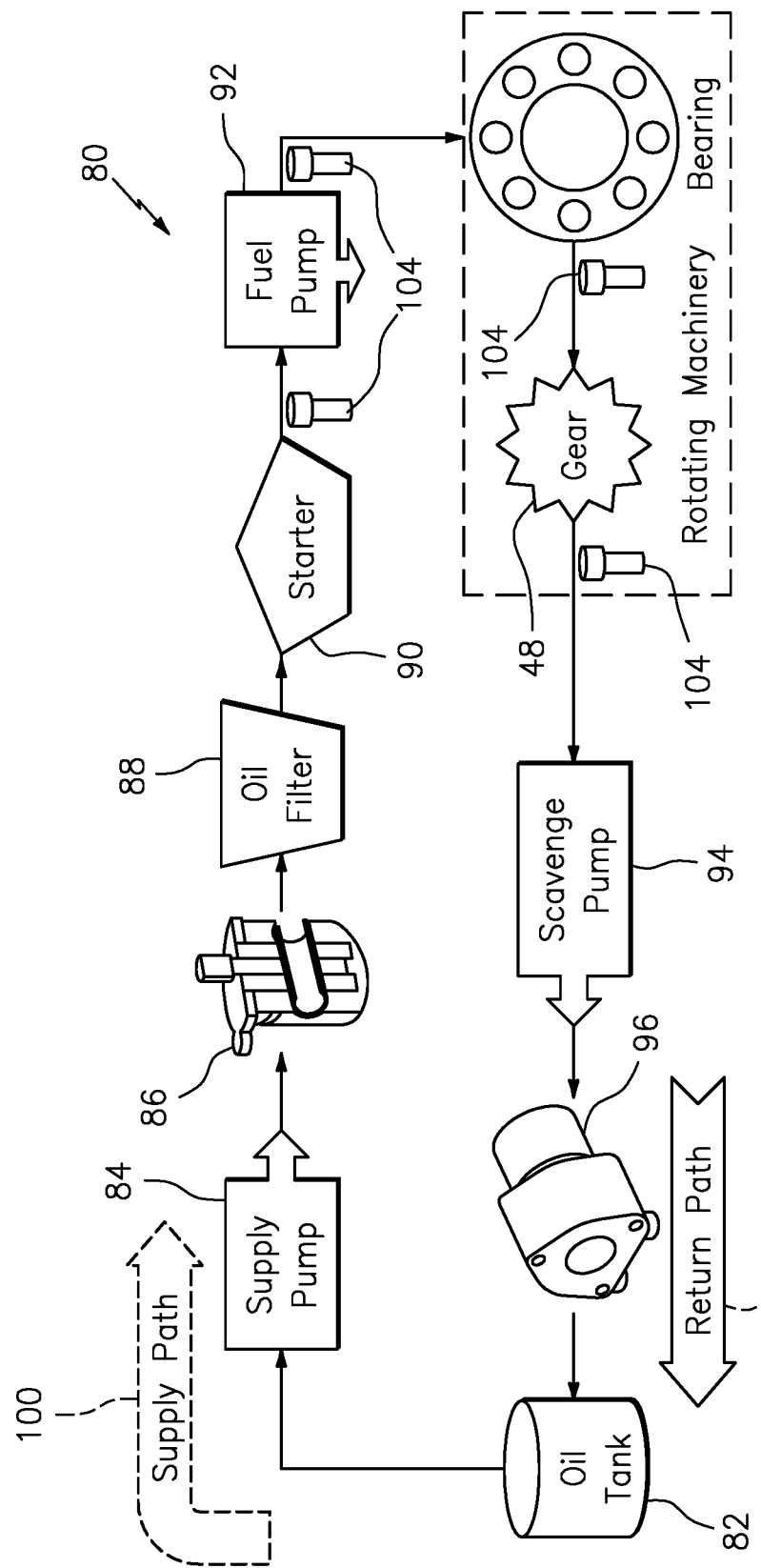
FIG. 3 is a schematic diagram of an oil system for a geared architecture gas turbine engine.

With reference to FIG. 3, an oil system 80 is schematically illustrated in block diagram form for the geared architecture 48 as well as other components which receive oil. It should be appreciated that the oil system 80 is but a schematic illustration and is simplified in comparison to an actual oil system. The oil system 80 generally includes an oil tank 82, a supply pump 84, an oil debris monitoring sensor 86, an oil filter 88, a starter 90, a fuel pump 92, the geared and bearing architecture 48, a scavenge pump 94, and an oil debris monitoring sensor 96 at an alternative location. The oil debris monitoring sensor 86, 96 could be a single sensor or a set of sensors placed in branched oil paths. The oil flow to the geared and bearing architecture 48 may be considered an oil supply path 100, and the oil flow from the geared and bearing architecture 48 can be considered an oil return path 102. Multiple of chip collectors 104 may be located in the supply path 100 and the return path 102 to capture ferrous debris.

The sensors 86, 96 historically utilize two field coils, excited by high frequency alternating current, to cause equal and opposing magnetic fields (M-field). The ferrous particle strength of the M-field created by one field coil after another, causes the processed signal to be a period of a sine wave. The nonferrous particle weakens the M-field created by one field coil after another, causing the similar sine wave but in opposing polarity. Generally, the signal magnitude is proportional to the size of particle and the signal width is inversely proportional to the particle speed.

Figure 4:
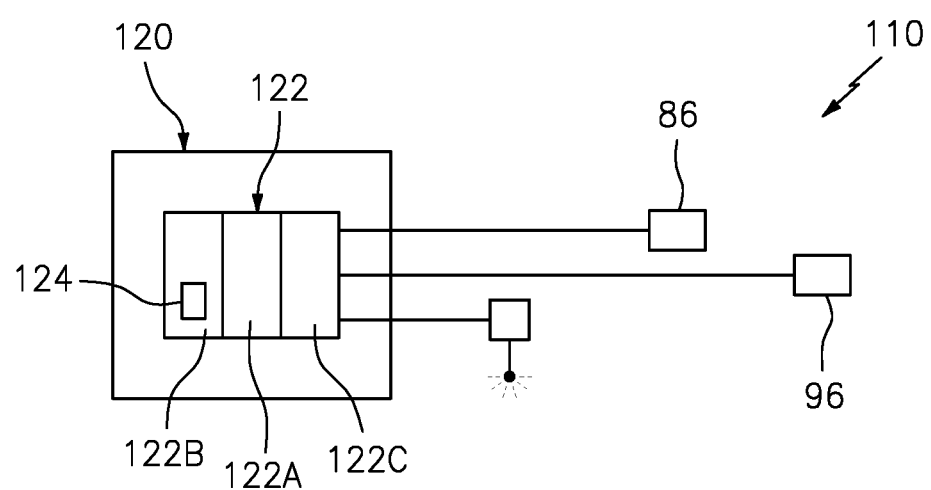
FIG. 4 is a schematic diagram of a debris detection system according to one disclosed non-limiting embodiment.

With Reference to FIG. 4, a debris detection system 110 generally includes a controller 120 in communication with the sensors 86, 96. The sensors 86, 96 may be in-line oil debris monitor sensors. The debris detection system 110 protects against unexpected phase angle changes which may affect individual oil debris monitors caused by replacement or redesign of other components in the system, such as a signal wire harness, that can drastically influence the phase angle.

The controller 120 generally includes a control module 122 that executes logic 124 to actively calculate and monitor the oil debris liberated in the oil system with regards to particle detection, mechanical system fault alert, and sensing system health. The functions of the logic 124 are disclosed in terms of functional block diagrams, and it should be appreciated that these functions may be enacted in either dedicated hardware circuitry or programmed software routines capable of execution in a microprocessor-based electronics control embodiment. In one example, the control module 122 may be a portion of a flight control computer, a portion of a Full Authority Digital Engine Control (FADEC), a stand-alone unit, or other system.

The control module 122 typically includes a processor 122A, a memory 122B, and an interface 122C. The processor 122A may be any type of known microprocessor having desired performance characteristics. The memory 122B may be any computer readable medium which stores data and control algorithms such as the logic 124 as described herein. The interface 122C facilitates communication with other components such as the sensors 86, 96, as well as remote systems such as a ground station, Health and Usage Monitoring Systems (HUMS), or other system.

The oil debris monitor phase angle is used to classify detected particle types (ferrous/nonferrous) through a mathematical transformation. The phase angle is calibrated by pulling a particle of known type and size through the sensor and using the ratio of I and Q channel amplitude and trigonometric relationships to calculate an optimum (for classification) phase angle. The I channel is the In-phase, or real component and the Q channel is the Quadrature (90° shift of real component) to provide a health assessment that may include, for example, particle count, particle type classification, size and mass estimates, sensing system availability, debris count rates, and other metrics.

Figure 5:
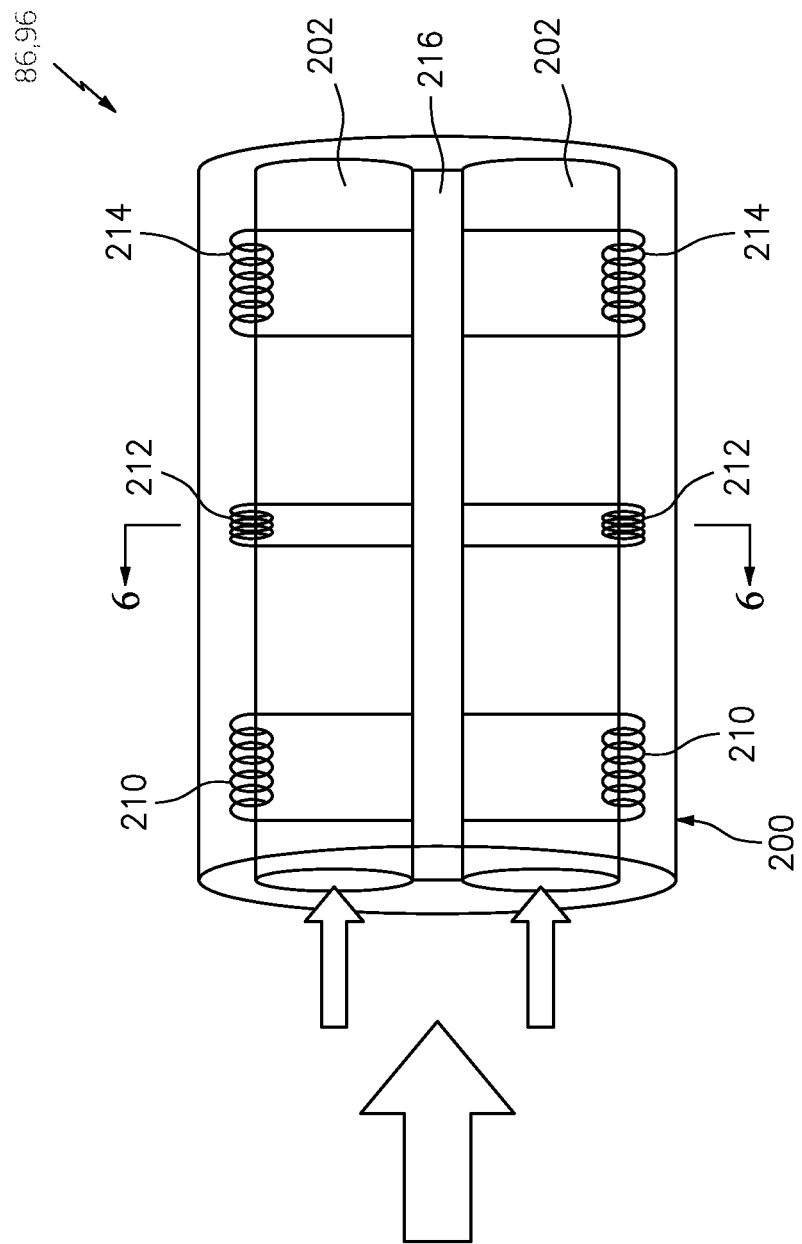
FIG. 5 is a schematic view of a multi-passage oil debris monitoring sensor.
Figure 7:
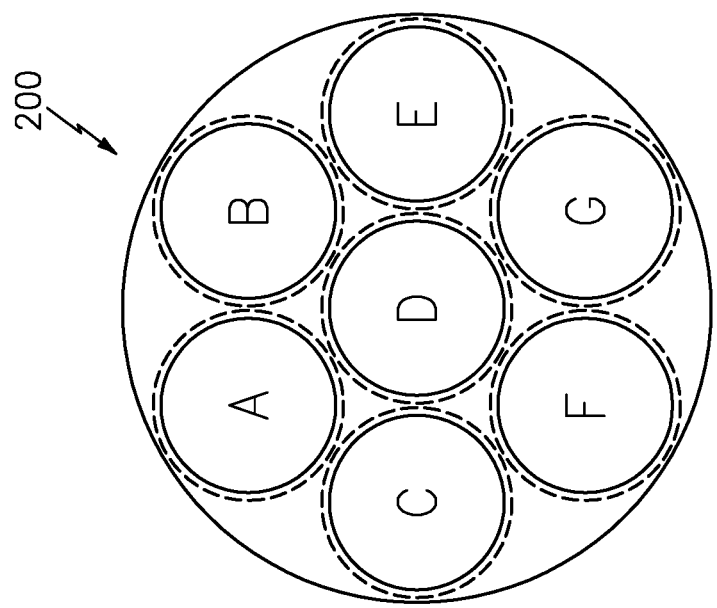
FIG. 7 is a schematic cross-section of the multi-passage oil debris monitoring sensor with multiple passages.
Figure 6:
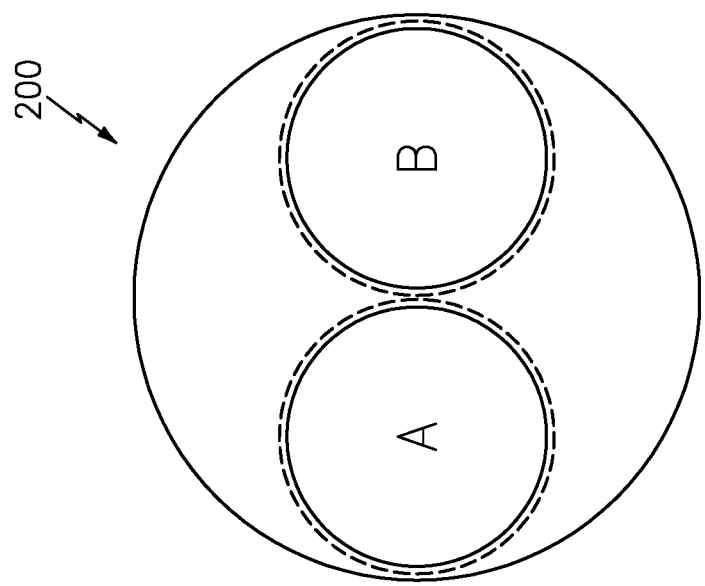
FIG. 6 is a schematic cross-section of the multi-passage oil debris monitoring sensor of FIG. 5 with two passages.
Figure 8:
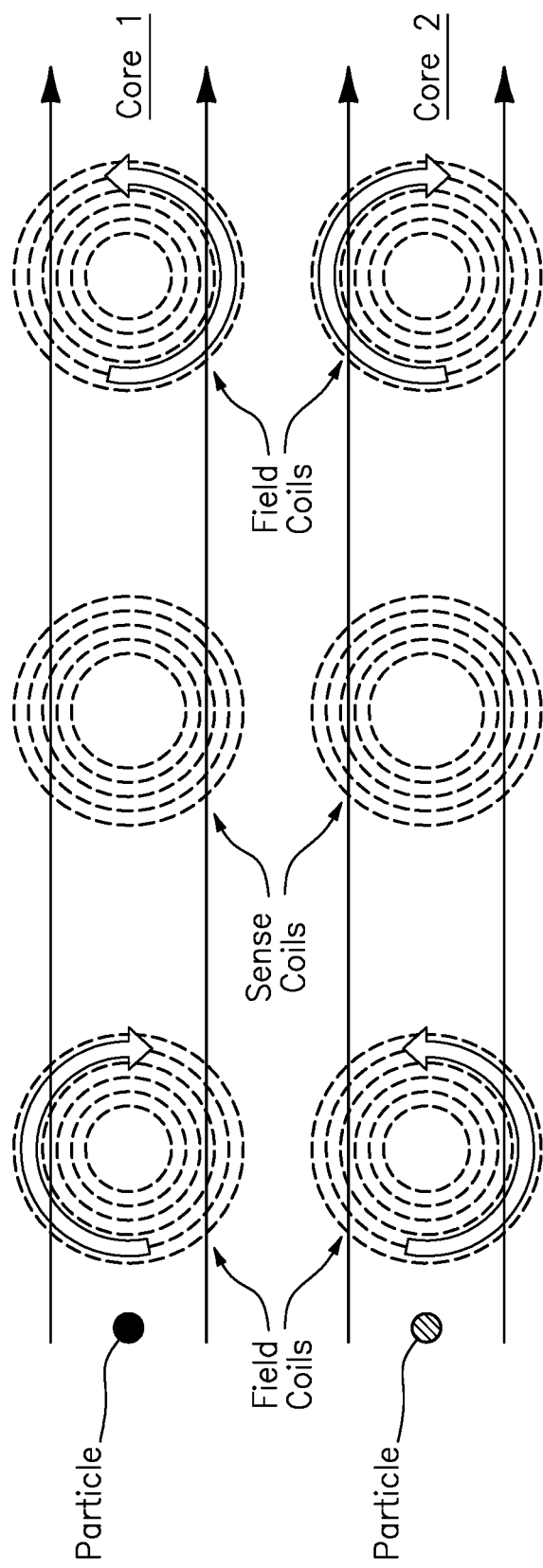
FIG. 8 is a representation of the field coil magnetic field directions of the multi-passage oil debris monitoring sensor of FIG. 5 with two passages.

With reference to FIG. 5, the oil debris monitoring sensors 86, 96 each generally include a housing 200 that contains a multiple of passages 202 (two shown as A and B flow paths in FIG. 6 and seven shown as A-G flow paths in FIG. 7). Each of the multiple of passages 202 are surrounded by a respective first field coil 210, a sense coil 212, and a second field coil 214 along the axis of each. In the illustrated FIG. 6 example of a two flow passage 202 arrangement, each flow passage 202 may have a set of field coils that are wound in opposing directions to minimize cross coil interference between the A and B flow paths and also for algorithmic isolation of particle path. Ideally, the generated magnetic fields are of relatively equivalent magnitude and frequency (FIG. 8-12).

A reduced diameter sensor bore 212 increases the signal to noise ratio for a given particle as compared to a larger bore and thereby increases the sensitivity to significantly smaller particles and achieves this capability without increasing the back pressure on the lube system to unacceptable levels for a given volumetric flow rate. This avoids increasing the differential pressure and producing a back pressure in the system which exasperates active systems in the fluidic circuit.

A dielectric 216 may be located between one or more of the multiple of passages 202. The dielectric, intended to reduce or prevent electromagnetic interferences, may not completely shield the interaction between the magnetic fields around each bore. As such, some parsing can be achieved by setting a minimum threshold in passage B based on the influence of the largest allowed particle in passage A and vice versa. If an excitation in passage B is greater than the above mentioned threshold, a particle must be present. If an excitation is less than the minimum threshold, it must be a reflection of a particle passing through channel A. In other embodiments, isolation can be performed via pulsing the field coils 210, 214 at different frequencies, staggering passages that cause deformation of the signal caused by the influence of the other passage, or combinations thereof.

Figure 13:
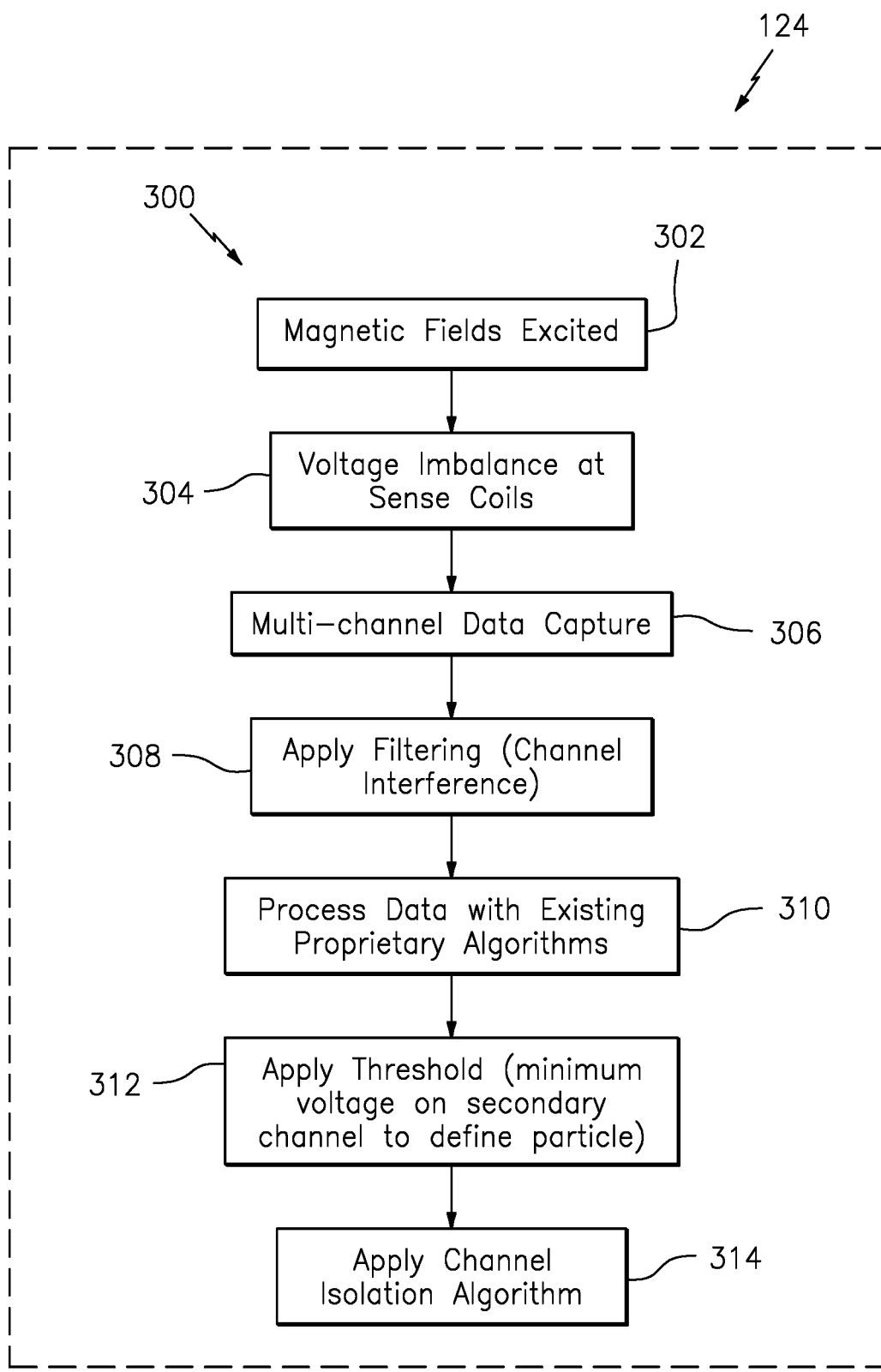
FIG. 13 is a block diagram representative of logic for the multi-passage oil debris monitoring sensor.

With reference to FIG. 13, a method 300 for the management of the interaction between the fields of the multiple of passages 202 so as to assure a proper count of particles that simultaneously pass through multiple passages of each oil debris monitoring sensor 86, 96 initially includes excitation of the first and second field coil 210, 214 in each of the multiple of passages 202 (302). Then, during operation, passage of one or more particles, any voltage imbalance is identified in the sense coil 212 in each of the multiple of passages 202 (304). The voltage imbalance data is then captured (306) and filtered (308). The data from the primary passage (e.g., the passage or lane through which the particle is passing, see FIGS. 9 and 10) is then processed with existing proprietary algorithms (310).

A threshold is then applied (312) to determine the minimum voltage on one or more of the secondary passages to define if a particle is also passing through the one or more secondary passages (314) in addition to the primary passage to properly identify the number of particles sensed. That is, whether multiple particles are passing though both passages (e.g., FIG. 11). or a single particle has passed through a single lane (e.g., FIG. 9, 10, 12). The ability to detect particles passing through a single sensor coil or multiple sensor coils depends on a threshold as defined by a magnitude and other parameters that define the particle signature (e.g., dashed horizontal lines in FIG. 9-12). This threshold can be determined by calibration of the system as it relates to the detection requirements of the system. The threshold can be fixed by the largest expected particle in system where the interference signal would be no greater than the smallest particle that needs to be detected. If there is system where the largest particle interference can be greater than the minimum detectable particle size, the minimum interference threshold can be adaptive to the dominant signal excitation (i.e. a particle of given size X will generate an interface signal of no greater than Y on any other channel, where Y is a function of any X sense).

Figure 9:
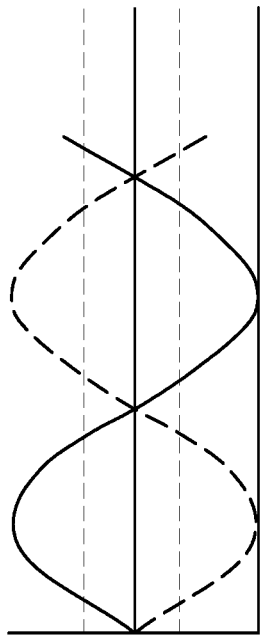
FIG. 9 is a signal representation of a particle passing through passage one only of the FIG. 8 multi-passage oil debris monitoring sensor of FIG. 5 with two passages.
Figure 11:
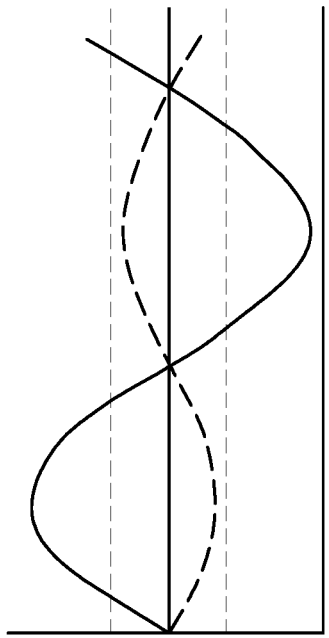
FIG. 11 is a signal representation of a particle passing through both passages of the FIG. 8 multi-passage oil debris monitoring sensor of FIG. 5 with two passages.
Figure 10:
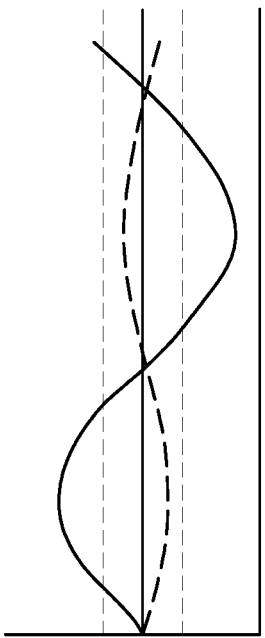
FIG. 10 is a signal representation of a particle passing through passage two only of the FIG. 8 multi-passage oil debris monitoring sensor of FIG. 5 with two passages.
Figure 12:
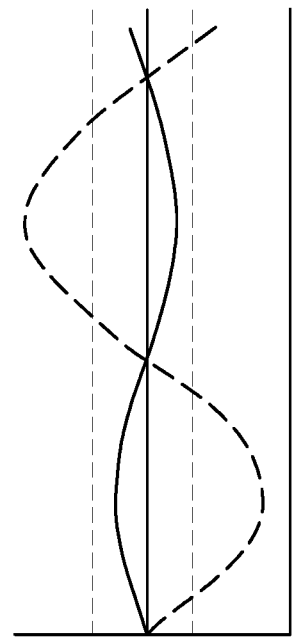
FIG. 12 is a signal representation of a larger particle passing through passage one of the FIG. 8 multi-passage oil debris monitoring sensor of FIG. 5 with two passages.

Finally, a channel isolation algorithm is applied if the minimum voltage is not identified (314). To ensure particle isolation to a specific passage (assuming the primary passage has the particle) a minimum amplitude has to be detected in one or more secondary passages along with a range signal defining parameters matching to assess the signal in the secondary passage to be a separate particle than that what is in the primary passage (if signals are time aligned). In the case of a dual-bore sensor, if a particle passes through a single channel, there will be a threshold exceedance in the processed signal of that channel. Any interference may leak to the other channel, but is just a reflection and does not breach the detection threshold (FIG. 9, 10, 12). If a particle passes through both channels simultaneously, the minimum threshold will be breached on each channel and the system will process the data as if two particles are present (FIG. 11).

Figure 14:
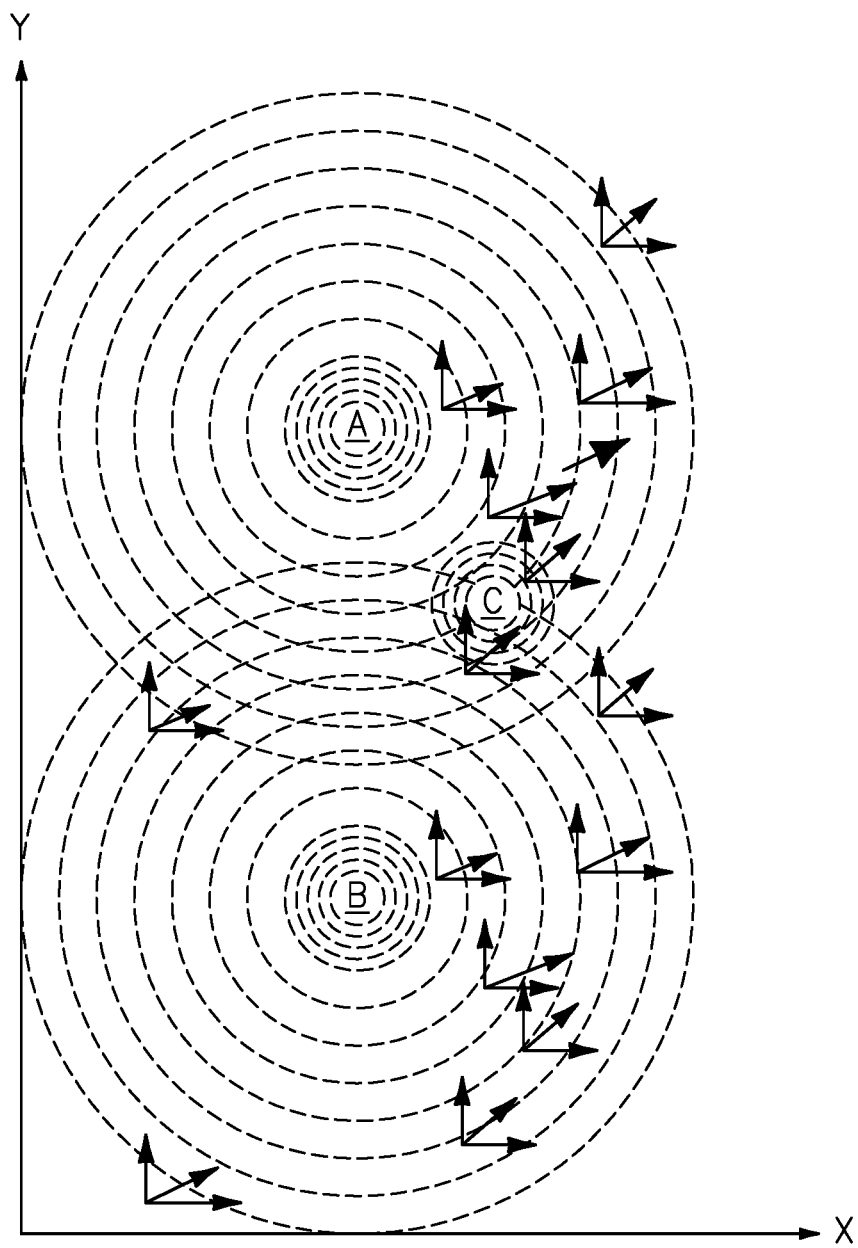
FIG. 14 is a schematic representation of a calculated interference at an example point C in between two magnetic fields of the multi-passage oil debris monitoring sensor of FIG. 5 with two passages.

A particle entering field A (e.g., primary passage) will also be reflected in field B (e.g., secondary passage) as a form of what is seen in the primary passage (signal shape defined by set of parameters). For example, with reference to FIG. 14, the electromagnetic field created by the field coils can be represented by Maxwell's third equation.

$$\nabla \times E = -\partial B / \partial t$$

$$B(x, y, z, t) = \begin{bmatrix} Bx(x, y, z, t) \\ By(x, y, z, t) \\ Bz(x, y, z, t) \end{bmatrix}$$

At any axial point z0 and a given time t0, the magnetic flux can be represented as a 2D vector as: B(x,y, z0,t0) . . . . Hence, the resulting magnetic strength can be assessed and represented by a set of vectors in a given coordinate. Let A and B represent activated field coils creating a magnetic field:

$$B(x, y, z, t) = \begin{bmatrix} Bx(x, y, z0, t0) \\ By(x, y, z0, t0) \\ Bz(x, y, z0, t0) \end{bmatrix}$$

The magnetic fields A and B produce interfering electromagnetic fields at an example point C such that resultant field at C will be the vector summation of the fields produced by A and B. This provides for the management of the interaction between the fields so as to assure a proper count of particles is provided should, for example, multiple particles simultaneously travel through the passages.

The oil debris monitoring sensors 86, 96 enhance system capability within the confines of the existing space reducing the sensing coil diameter, increasing the signal to noise ratio for a given particle as compared to a larger bore single sensor, increasing the sensitivity to significantly smaller particles, and achieve this capability without increasing the back pressure in the system for a given volumetric flow rate. In addition, the sensor signal induced by interference from the other passage can be made much smaller than the signal due to particle passage by virtue of the spatial relationship of the coils and by installing some degree of shielding. There may be still risk of missing detection of small particles if a very large particle passes through the system simultaneously with a small particle, but the benefit of having an unintrusive sensor with adequate sensitivity for high thrust engines outperforms such risk, as a single large bore sensor detection capability loss is fixed and thus more severe. The oil debris monitoring sensors 86, 96 meets sensing capability, back pressure, weight, and the cost needs associated with sensing technology maturation for aviation applications.

Although particular step sequences are shown, described, and claimed, it should be appreciated that steps may be performed in any order, separated or combined unless otherwise indicated and will still benefit from the present disclosure.

The foregoing description is exemplary rather than defined by the limitations within. Various non-limiting embodiments are disclosed herein; however, one of ordinary skill in the art would recognize that various modifications and variations in light of the above teachings will fall within the scope of the appended claims. It is therefore to be appreciated that within the scope of the appended claims, the disclosure may be practiced other than as specifically described. For that reason, the appended claims should be studied to determine true scope and content.

What is claimed:

1. An oil debris monitoring sensor, comprising:
a housing; and
a multiple of passages within the housing, each of the multiple of passages surrounded by a set of coils for particle detection, wherein each set of coils comprises a respective first field coil, a sensor coil, and a second field coil.

2. The oil debris monitoring sensor as recited in claim 1, wherein the multiple of passages within the housing comprises two or more passages.

3. The oil debris monitoring sensor as recited in claim 1, wherein the housing is located in-line with an oil flow path that is in communication with a geared architecture of a gas turbine engine.

4. The oil debris monitoring sensor as recited in claim 1, wherein a first set of coils around a first passage of the multiple of passages are wound in a different direction than a second set of coils around a second passage of the multiple of passages.

5. The oil debris monitoring sensor as recited in claim 4, further comprising a dielectric between the first passage and the second passage.

6. An oil debris monitoring sensor, comprising:
a housing; and
a first passage within the housing along a first axis;
a first field coil, a sensor coil, and a second field coil around the first passage and along the first axis;
a second passage within the housing along a second axis parallel to the first axis; and
a first field coil, a sensor coil, and a second field coil around the second passage and along the second axis.

7. The oil debris monitoring sensor as recited in claim 6, wherein the housing is located in-line with an oil flow path that is in communication with a geared architecture of a gas turbine engine.

8. The oil debris monitoring sensor as recited in claim 6, wherein a first magnetic field generated by the first field coil around the first passage is in a first direction and a second magnetic field generated by the first field coil around the second passage is in a second direction opposite the first direction.

9. The oil debris monitoring sensor as recited in claim 6, further comprising a dielectric between the first passage and the second passage.

10. A method for determining a presence of a particle in a system, comprising:
   a) locating a housing in-line with an oil flow path;
   b) communicating oil through a multiple of passages within the housing;
   c) detecting a particle through processing data from each passage; and
   d) isolating the particle to one of the multiple of passages within the housing wherein step d) comprises applying a channel isolation algorithm if a minimum voltage is not identified in response to the particular passing through the housing.

11. The method as recited in claim 10, further comprising locating the oil flow path in communication with a geared architecture of a gas turbine engine.

12. The method as recited in claim 10, wherein step d) comprises generating a first magnetic field around a first passage in a first direction and generating a second magnetic field around a second passage in a second direction opposite the first direction.

13. The method as recited in claim 10, wherein step d) comprises determining an interference between a magnetic field associated with a first passage and a magnetic field associated with a second passage in response to the particle passing through the housing.

14. The method as recited in claim 10, wherein step d) comprises determining whether a minimum amplitude in a second passage is within a predetermined range, and assessing whether a second particle is passing through the second passage.

15. A method for determining a presence of a particle in a system, comprising:
   a) locating a housing in-line with an oil flow path;
   b) communicating oil through a multiple of passages within the housing;
   c) detecting a particle through processing data from each passage; and
   d) isolating the particle to one of the multiple of passages within the housing, wherein step d) comprises applying a channel isolation algorithm if a minimum voltage is not identified.

\* \* \* \* \*